(12) United States Patent
Jenkins et al.

(10) Patent No.: US 8,858,959 B2
(45) Date of Patent: Oct. 14, 2014

(54) GEL VACCINE DELIVERY SYSTEM FOR TREATING POULTRY

(75) Inventors: Mark C. Jenkins, Davidsonville, MD (US); Raymond H. Fetterer, College Park, MD (US); Joseph T. Persyn, San Antonio, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/546,455

(22) Filed: Jul. 11, 2012

(65) Prior Publication Data
US 2013/0017220 A1 Jan. 17, 2013

Related U.S. Application Data

(60) Provisional application No. 61/508,146, filed on Jul. 15, 2011.

(51) Int. Cl.
*A61K 39/012* (2006.01)
*A61K 39/002* (2006.01)
*A61K 9/16* (2006.01)
*A61K 9/00* (2006.01)
*A61K 39/00* (2006.01)

(52) U.S. Cl.
CPC ............ *A61K 39/002* (2013.01); *A61K 39/012* (2013.01); *A61K 2039/54* (2013.01); *A61K 2039/542* (2013.01); *A61K 9/1658* (2013.01); *A61K 9/0056* (2013.01)
USPC ...................................... 424/271.1; 424/492

(58) Field of Classification Search
None
See application file for complete search history.

(56) References Cited

U.S. PATENT DOCUMENTS

| | | | |
|---|---|---|---|
| 4,438,097 A | 3/1984 | Shirley | |
| 4,544,548 A | 10/1985 | Davis et al. | |
| 4,552,759 A | 11/1985 | Davis et al. | |
| 5,006,341 A | 4/1991 | Davis et al. | |
| 5,068,104 A | 11/1991 | Bhogal et al. | |
| 5,597,564 A * | 1/1997 | Ying | 424/94.65 |
| 5,846,762 A | 12/1998 | Woodward | |
| 6,391,452 B1 * | 5/2002 | Antonsen et al. | 428/402.2 |
| 6,495,146 B1 | 12/2002 | Evans et al. | |
| 7,018,640 B2 | 3/2006 | Evans et al. | |
| 7,354,593 B2 | 4/2008 | McDougald et al. | |
| 7,794,836 B2 | 9/2010 | Vasishtha et al. | |
| 2005/0064027 A1 | 3/2005 | Jacob et al. | |
| 2010/0015182 A1 | 1/2010 | Lang et al. | |
| 2011/0081414 A1* | 4/2011 | Drouillard et al. | 424/463 |
| 2011/0091506 A1 | 4/2011 | Gibson et al. | |
| 2011/0217333 A1 | 9/2011 | Lee | |
| 2011/0314575 A1 | 12/2011 | Yusibov et al. | |

FOREIGN PATENT DOCUMENTS

EP 0134703 A1 * 8/1984

OTHER PUBLICATIONS

Nakamura et al (S.T.P. Pharma Sciences 8(1):67-73, 1998).*
Ding, X. et al., "In ovo vaccination with the *Eimeria tenella* EtMIC2 gene induces protective immunity against coccidiosis" 2005 Vaccine 23:3733-3740.
Jenkins, Mark C. et al., "Gel-Bead Delivery of *Eimeria* Oocysts Protects Chickens Against Coccidiosis", (2012) Avian Diseases 56(2):306-309.
Jenkins, Mark C. et al., "Differing Susceptibilities of *Eimeria acervulina*, *Eimeria maxima*, and *Eimeria tenella* Oocysts to Desiccation", (2013) Journal of Parasitology 99(5):899-902.
Jenkins, Mark C. et al., "Protecting Chickens Against Coccidiosis in Floor Pens by Administering *Eimeria* Oocysts Using Gel Beads or Spray Vaccination", (2013) Avian Diseases 57(3):622-626.
Norton, C. C. and L. P. Joyner, "Avian coccidiosis: the administration of encapsulated oocysts", (1986) Parasitology 92:499-510.

* cited by examiner

*Primary Examiner* — Patricia A Duffy
(74) *Attorney, Agent, or Firm* — Gail E. Poulos; David L. Marks; Lesley Shaw

(57) ABSTRACT

Safe and effective gel-bead vaccines for treating domesticated birds for diseases caused by cyst-forming protozoa, especially for coccidiosis.

42 Claims, 7 Drawing Sheets

GEL VACCINE DELIVERY SYSTEM FOR TREATING POULTRY

RELATED APPLICATIONS

This application is claims priority to U.S. Provisional Patent Application Ser. No. 61/508,146, filed Jul. 15, 2011 the contents of which are incorporated herein by reference in their entirety

BACKGROUND OF THE INVENTION

1. Field of the Invention

This invention relates to oral vaccines containing effective amounts of oocysts from cyst-forming protozoa for treating domesticated birds and to methods for using the oral vaccine for treating domesticated birds for diseases caused by cyst-forming protozoa.

2. Description of the Related Art

Avian coccidiosis is an intestinal disease primarily of poultry caused by protozoa in the genus *Eimeria*. Coccidiosis causes U.S. broiler producers an annual loss of over $ 350 million, with losses worldwide exceeding $ 1 billion. The disease has been controlled for decades by medication of feed with anti-coccidial drugs, but the appearance of drug-resistant strains of *Eimeria* and increased consumer pressure to reduce use of medicated feeds has prompted alternative control measures. Medication with several different anticoccidical drugs has been effective in preventing severe outbreaks of disease. However, the useful period of most of these drugs is limited because of the emergence of resistant strains of coccidia (Chapman, Vet. Parasitol., Volume 15, 11-27, 1984; Chapman, Res. Vet. Sci., Volume 38, 226-230, 1985; Jeffers, Avian Dis., Volume 18, 74-84, 1984; Long and Jeffers, Parasitol. Today, Volume 2, 236-238, 1986; Rose and Mockett, Paraite Immunol., Volume 5, 479-489, 1983). There has been success reported in preventing coccidiosis by immunizing chickens with nonviable extracts of infected tissues (McKenzie and Long, Poult. Sci, Volume 65, 892-897, 1986) and sporozoite antigen (Murray et al., In L. R. McDougald, L. P. Joyner, and P. L. Long (ed.), Research in avian coccidiosis. Proceeding of the Georgia Coccidiosis Conference 1985. University of Georgia Press, Athens, Ga., 1986). Although it is unclear what immune mechanism is responsible for establishing protection, it is known that both humoral (Danforth and Augustine, Poult. Sci, Volume 62, 2145-2151, 1988; Lillehoj and Ruff, Avian Dis., Volume 31, 112-119, 1987; Rose and Mockett, 1983, supra) and cell-mediated (Klesius and Hinds, Infect. Immun., Volume 26, 1111-1115, 1978; Lillehoj, Infect. Immun, Volume 55, 1616-1621, 1987; Morita et al., J. Psarasitol., Volume 59, 199-200, 1973; rose, Exp. Parasitol., Volume 42, 129-141, 1977; Rose and Hesketh, Infect. Imun, Volume 26, 630-637, 1979; Rose and Hesketh, J. Protozool., Volume 31, 549-553, 1984) immune responses are involved, with the latter playing a major role (Lillehoj, 1987; supra; Rose and Hesketh, 1979, supra; Rose et al., Parasite Immunol., Volume 19, 53-69, 1988).

One approach that has met with success is vaccination of day-old chicks with a mixture of low doses of virulent or attenuated *Eimeria* oocysts. Vaccination for coccidiosis is generally performed in the hatchery on the day of hatch by spraying live *Eimeria* vaccine directly onto the birds, or through injection directly into 18d embryos. The infective oocysts complete their life cycle inside the intestinal tract of the bird culminating with the release of a new generation of unsporulated oocysts in 5-11 days post-infection, the timeframe being dependent on the species of the *Eimeria*. The unsporulated oocysts excreted with the feces then become infective, i.e., sporulate, in the outside environment and reinfect susceptible birds through host ingestion. Depending on a number of factors (e.g. infection dose), the birds become immunized against coccidiosis. This immunity is characterized by a decrease and/or absence of parasites observed microscopically in the intestine, a reduction of the shedding of oocysts, a reduction of the intestinal lesions, a reduction of the clinical disease, and/or a reduction or prevention of weight loss. The acquired immunity wanes over a three to four month time period in the absence of subsequent exposure to infective oocysts.

Various types of vaccines and methods of vaccination are available for immunizing poultry against coccidiosis. Published U.S. Patent Application 2010/001518 A1, published Jan. 21, 2010 (Lang et al) teach a vaccine containing at least two different strains of a single species of a sporozoan *Coccida* genus. The publication discloses multivalent vaccines that comprise any and all *Coccidia* genuses. The publication teaches that the vaccine can be administered by any route including oral by eyedrop, intranasal, in feed, in water or by spray; in ovo, topically or by injection such as intravenous, subcutaneous, intramuscular, intraorbital, intraocular, intradermal, and/or intraperitoneal vaccine. The vaccine contains sporulated oocysts in potassium dichromate solution and diluted to the appropriate dose vaccine).

Patent application US2008/0190373, published Aug. 14, 2008 (Lee) teaches a method for spraying a soft gel form containing a therapeutic agent such as oocysts of *Eimeria* species as a plurality of beadlets that are sprayed directly onto chicks into a poultry hatchling tray containing hatchlings. The beadlets are consumed by the poultry hatchlings while in the hatchling tray. The publication discloses an edible temperature setting polysaccharide gel such as alginate or carrageenan powder is dissolved in water and contain an equal volume of a therapeutic agent such as an oocysts suspension. This gel composition is then placed in a dispensing apparatus and sprayed into the hatching trays. The spraying forms the beadlets. U.S. Pat. No. 7,354,593, issued Apr. 8, 2008 (McDougald et al.) discloses a vaccine for coccidiosis which contains a mixture of sporulated oocysts from precocious strains of *E. acervulina, E. maxima,* and *E. tenella*. The vaccine comprises sterilized oocysts suspended in a preservative consisting of phosphate buffered saline containing gentamicin, or in sterile distilled water containing a suspending agent such as gum, a cellulose derivative, a microcrystalline cellulose, carageenan, sodium alginate, pectin or starch, a polypeptide suspending agent such as gelatin; a synthetic polymer suspending agent such as polyacrylic acid or a silicate suspending agent such as magnesium aluminum silicate. These vaccines were administered by spraying the birds or by oral gavage.

U.S. Pat. No. 7,018,640, issued Mar. 28, 2006 (Evans et al.) discloses an in ovo vaccine for coccidiosis that included live *Eimeria* sporozoites or merozoites or a mixture of both in any physiologically suitable medium that is injected into the poultry egg during the final quarter of incubation.

U.S. Pat. No. 5,006,341, issued Apr. 9, 1991 (Davis et al.) discloses an oral vaccine that is a dry free flowing solid beadlet of a lipid-continuous emulsion containing about 25% to about 50% by weight water in a lipid such as hardened palm kernel oil and viable encysted protozoa such as a sporulated oocyst of a species of coccidium. The beadlet also includes a protective coating of animal feed, cement, and/or gypsum. The beadlets can be blended with feed ingredients to provide a composite feed formulation.

U.S. Pat. No. 5,068,104, issued Nov. 26, 1991 (Bhogal et al.) discloses an oral vaccine for coccidiosis which includes suspensions of excysted sporozoites in physiologically balanced medium containing water-soluble polymeric stabilizers such as gels, gelatins, polysaccharide gums, cellulose or cellulose derivatives which extend viability and storage. U.S. Pat. No. 4,552,759, issued Nov. 12, 1985 (Davis et al.) discloses a composition for control of coccidiosis where oocysts are added directly during the mixing of poultry feed or via a premix which is a solid free-flowing dry composition or it can be a paste or slurry with water for incorporation into poultry feedstuff by mixing or spraying.

While various vaccines and delivery systems have been developed for immunizing domesticated birds, there remains a need in the art for an effective vaccine and delivery system for the domesticated bird industry. The present invention described below includes a new delivery system for coccidiosis vaccines using gel bead technology that provides efficacious and safe vaccines which are different from related art vaccines and delivery systems.

SUMMARY OF THE INVENTION

It is therefore an object of the present invention to provide an effective vaccine delivery system for treating domesticated bird hatchlings.

Another object of the present invention is to provide a vaccine delivery system that includes a gelatin, a diluent, a humectant, and an effective amount of oocysts from a cyst-forming protozoa.

A still further object of the present invention is to provide a vaccine delivery system that includes flavored gelatin, a humectant, a diluent, and an effective amount of *Eimeria* oocysts to control coccidiosis in domesticated birds.

A still further object of the present invention is to provide a vaccine delivery system that includes flavored gelatin, unflavored gelatin, a diluent, a humectant, and an effective amount of *Eimeria* oocysts to control coccidiosis in domesticated birds and further includes a structuring agent that provides added structure to the gel bead while decreasing oxygen and/or water loss.

A still further object of the present invention is to provide a vaccine delivery system that includes flavored gelatin, unflavored gelatin, a diluent, a humectant, and an effective amount of *Eimeria* oocysts to control coccidiosis in domesticated birds and further includes a structuring agent wherein said structuring agent is selected from the group consisting of, but not limited to, clay, such as bentonite, montmoilonite, attapugite, terramine, kaolin, saponite, laponite, French-green, Fuller's earth, and the like; silicates, such as layered magnesium aluminum silicate platelets, micas, talc, diatomaceous silicates, precipitated silicas, fumed silicas, hydrophilic silicates, and hydrophobic silicates; starches, such as hydrophobic starch molecules; phospholipids; pillared or pillared-like materials; metal salts, such as nano-sized platelets of metal salts; and mixtures thereof.

Another object of the present invention includes adding a structuring agent to the vaccine delivery system in an amount of about 0.1% to about 50% by weight of the gelatin.

Another object of the present invention is to provide a vaccine delivery system includes a gelatin, a diluent, a humectant, and an effective amount of *Eimeria* oocysts to control coccidiosis in domesticated birds and is coated with an edible coating such as for example, methylmethacrylates such as Eudragit® (Rohm and Hass) and Kollicoat® (BASF); zein, cellulose derivates (cellulose acetate, cellulose phthalate, hydroxylpropylmethylcellulose, ethylcellulose), shellac, fats and waxes.

Another object of the present invention is to provide a vaccine delivery system that includes a gelatin, a diluent, a humectant, a structuring agent and an effective amount of *Eimeria* oocysts to control coccidiosis in domesticated birds and is coated with an edible coating such as for example, methylmethacrylats such as Eudragit® (Rohm and Hass) and Kollicoat® (BASF); zein, cellulose derivates (cellulose acetate, cellulose phthalate, hydroxylpropylmethylcellulose, ethlcellulose), shellac, fats and waxes.

Another object of the present invention is to provide a vaccine delivery system that includes an unflavored gelatin, a diluent, a humectant, a structuring agent and an effective amount of *Eimeria* oocysts to control coccidiosis in domesticated birds and is coated with an edible coating such as for example, methylmethacrylats such as Eudragit® (Rohm and Hass) and Kollicoat® (BASF); zein, cellulose, acetate, cellulose phthalate, hydroxylpropylmethylcellulose.

Another object of the present invention is to provide a method for controlling coccidiosis in animals that includes delivering a vaccine delivery system that is a gel-bead made of gelatin, a diluent, a humectant, and oocysts from at least one cyst-forming protozoa which vaccinates animals against diseases caused by cyst-forming protozoa.

Another object of the present invention is to provide a method for controlling coccidiosis in animals that includes delivering a vaccine delivery system that includes a gelatin, a diluent, a humectant, a structuring agent and an effective amount of *Eimeria* oocysts to control coccidiosis and is coated with an edible coating such as for example, methylmethacrylates such as Eudragit® (Rohm and Hass) and Kollicoat® (BASF); zein, cellulose derivatives such as cellulose acetate, cellulose phthalate, hydroxylpropylmethylcellulose, ethylcellulose, for example, fats and waxes.

Further objects and advantages of the present invention will become apparent from the following description.

DETAILED DESCRIPTION OF THE INVENTION

Figure 1:
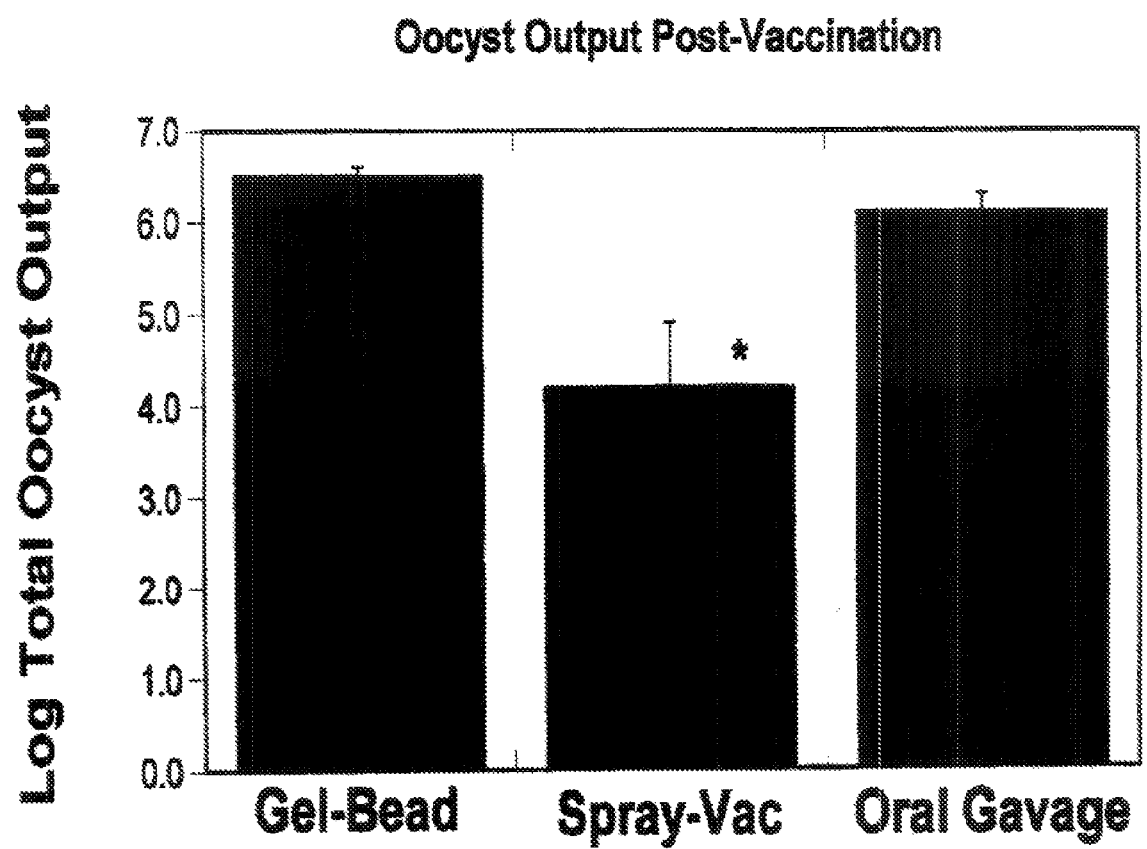
FIG. 1 is a graph showing average total *Eimeria* oocysts output between days 5-8 post-immunization in week-old broiler chickens vaccinated with a mixture of *Eimeria acervulina, Eimeria maxima*, and *Eimeria tenella* oocysts by 3 different delivery methods-gel-beads, spray-vaccination, or oral gavage.

The present invention relates to an alternative system for delivering live oocysts from cyst-forming protozoa, especially *Eimeria* protozoa, in vaccines to animals, especially domesticated birds, using gel-beads. While coccidiosis vaccines are gaining acceptance, there are several issues related to their use, including lower productivity in vaccinated flocks. The gel-beads of the present invention are spread onto feed the same day that chicks are delivered from the hatchery. Once in bird housing, especially poultry houses, newly hatched chicks are attracted to the vaccine gel beads and ingest the vaccine.

The term domesticated bird(s) includes chicken, turkeys, ducks, game birds including but not limited to quail, pheasants, and geese, and ratites including but not limited to ostrich.

The term "poultry" denotes birds of the order Galliformes such as for example, ordinary domestic fowl.

Different species of poultry suffer from infections caused by different coccidian species. The domestic fowl, *Gallus domesticus*, can be infected by any of the coccidian *Eimeria tenella, E. necatrix, E. brunetti, E. maxima, E. acervulina*, and *E. praecox*. Turkey (*Meleagris*) can be infected with *Eimeria melagrimitis, E. dispersa, E. meleagriditis, E. gallopavonis, E. adenoides, E. innocua* and *E. subrotunda*. Domestic ducks (*Anas*) can be infected by *Tyzzeria perniciosa* and *E. anatis* which they can acquire from wild ducks (*Anas platyrhyncos*). Geese (*Anser*) can be infected with *E. anseris, E. nocens*, and *E. parvula*, and in addition domestic geese can become infected with *E. hermani, E. striata*, and *E. fulva* by association with Canadian geese.

Coccidiosis also occurs in other animals and the invention can be used to control coccidiosis in any avian or non-avian neonatal animal such as pigs, ruminants such as cattle, sheep, and goats, and rabbits, for example.

The composition of the present invention can also be used to prepare vaccines for other cyst-forming parasitic protozoa.

Vaccine is defined herein in its broad sense to refer to any type of biological agent in an administrable form capable of stimulating a protective immune response in an animal inoculated with the vaccine. For purposes of the present invention, the vaccine may comprise one or more live strains of *Eimeria*.

More specifically the vaccine comprises oocysts of live strains of *Eimeria*. The vaccine can also be a combination of different *Eimeria* species such as, for example, *E. acervulina, E. maxima, E. tenella*, etc. These three species are present in all commercially available vaccines.

Effective immunization or vaccination dose or dosage is defined herein as being the amount that will induce complete or partial immunity in a vaccinated animal against a subsequent challenge by a virulent strain.

Efficacious vaccine is defined herein as a vaccine that offers equal or greater than about 90% protection against pathogen infections.

The term effective amount refers to the ability of the vaccine to induce an immune response suitable and sufficient to have the desired effect such as the treatment or prevention of coccidiosis.

The term vaccination and vaccinating means the inoculation of a substance or composition (a vaccine) into the body of a subject for the purpose of producing immunity against a disease, such as coccidiosis, that is for the purpose of treating or preventing a disease. Accordingly, vaccination may be therapeutic or prophylactic. By therapeutic vaccination is meant the administration of a vaccine to an animal already suffering from a disease such as coccidiosis, typically for the purpose of heightening or broadening the immune response to thereby halt, impede, or reverse the progression of the disease. The terms vaccination and immunization are used interchangeably herein. Similarly, the terms vaccination and administration are used interchangeably herein.

The term structuring agent is defined as a substance which decreases oxygen and/or water permeation and/or loss through the gel based delivery system of the present invention (U.S. Pat. No. 7,794,836, Vasishtha et al, Sep. 14, 2012; herein incorporated by reference in its entirety). The structuring agent can be selected from the group consisting of, but not limited to, clay, such as bentonite. montmorillonite attapugite, terramine, saponite, laponite, French-green. Fuller's earth, and the like; silicates, such as layered magnesium aluminum silicate platelets, micas. talc, diatomaceous silicates, precipitated silicas, fumed silicas, hydrophilic silicates, and hydrophobic silicates; starches, such as hydrophobic starch molecules; phospholipids; pillared or pillared-like materials; metal salts, such as nano sized platelets of metal salts; and mixtures thereof. In the present invention the preferred structuring agent should be generally acceptable as safe (GRAS) such as bentonite or terramine as these materials are generally recognized as safe and/or are approved for use in edible compositions. Generally the structuring agent is present in an amount of from about 0.1 to about 50% by weight of the gelatin.

The gel beads can be made using a commercially available flavored gelatin, an unflavored gelatin such as for example bovine gelatin, or mixtures of the two.

The vaccine delivery system of the present invention includes a humectant such as, for example, glycerin to stabilize animal cell structure, plasticize the gelatin and to serve as a humectant. Any substance which stabilizes animal cell structure, plasticizes gelatin and promotes retention of water is useful in the present invention. Other humectants include, for example, sugar alcohols (i.e. sorbitol), propylene glycol, polyglycols and salts. An effective amount is defined as that amount which will allow living cells to remain viable in the vaccine delivery system. Suitable effective amounts can be determined readily by one of ordinary skill in the art. Glycerin added at 25% up to 70% weight/volume ratio of the composition is a preferred effective amount. Additional humectants may include sugar alcohols (i.e. sorbitol), propylene glycol, polyglycols and salts.

The vaccine delivery system can be prepared with gelatin alone or gelatin and a structuring agent. The vaccine delivery system is made up of flavored gelatin, unflavored gelatin and mixtures thereof. An effective amount of gelatin is an amount that permits the formation of beads, and prevents water loss, and does not break easily once a bead is formed. The weight range of approximately 9 to approximately 11% w/v is a preferred effective range of gelatin in the vaccine delivery system. Based on solids, gelatin is used at a concentration of at 30% or higher.

The gel beads were prepared by dissolving the gelatin in hot deionized water, about 95-100 degrees centigrade and allowing the gelatin to completely dissolve followed by cooling to about 35 degrees C. while continuously stirring. Sporulated oocysts from cyst forming protozoa were added to the approximately 35 degree centigrade water-gelatin mixture and stirred for approximately one minute after addition. Oocysts can be from a single species or a mixture of species. In the case of *Eimeria* it is preferred to use at least *E. acervulina*, *E. maxima*, and *E. tenella* sporulated oocysts as is common in commercially available vaccines. An effective amount of oocytes are added to the water-gelatin mixture wherein said amount is an amount that will induce complete or partial immunity in a vaccinated animal against a subsequent challenge by a virulent strain. The determination of which is well within the ordinary skill in the art. A preferred range of oocytes is approximately $1.5 \times 10^3$ to $10^4$ total oocysts with *E. maxima* comprising approximately 5% to approximately 40% of the total inoculum.

If a structuring agent is used, it is mixed with diluents such as deionized water, brought to about 90 degrees with continuous stirring and then cooled to approximately 60 degrees C. After reaching approximately 60 degrees C., the flavored, unflavored or mixture of flavored or unflavored gelatin is added. If unflavored gelatin is used alone, red or green food dye is added to the mixture with the gelatin. Glycerin is added to achieve a 25%-75% w/v ratio. After the contents dissolved, an aliquot of the mixture was removed and allowed to cool to approximately 40 degrees centigrade and an effective amount of sporulated oocysts from cyst forming protozoa was added, suspended in a volume of approximately 0.1 ml of the cooled mixture and then added to the approximately 40 degree C. gel solution, mixed by rapid inversion.

The gel mixture including oocysts was then added dropwise to ice-cold mineral oil or vegetable oil that was continuously stirred. Gel beads form immediately upon hitting the ice-cold oil and settle to the bottom of the oil containing container. After the desired amount of beads are formed, the excess oil is removed from the beads and the bead slurry is stored at approximately 4 degrees centigrade until use. The beads can be stored for at least 3-4 months at 4 degrees C.

Another aspect of the invention is to coat the gel beads with an edible coating to prolong the shelf life of the beads. Any edible coating can be used as long as it does not negatively affect the function of the vaccine. Examples of useful coatings in the present invention include methylmethacrylates including, for example, Eudragit® (Rohm and Hass) and Kollicoat® (BASF); zein, cellulose derivates (cellulose acetate, cellulose phthalate, hydroxylpropylmethylcellulose, ethylcellulose), fats and waxes. The beads are overcoated by spraying the coating material, dissolved in an appropriate solvent or as a hot-melt, onto the beads using equipment known to one skilled in the art such as an air-suspension coater or pan coater. The coating thickness can be controlled to tailor the level of added protection.

The beads of the present invention have preferable dimensions of approximately 2 mm to 5 mm in diameter, with 2-3 mm preferable. Formation of the gel beads with the stated diameter is well within the ordinary skill in the art given the description of the present invention.

Approximately 25 ml of beads are distributed onto approximately 300 cm$^2$ area on the surface of poultry feed.

The number of oocytes inoculated and volume of gelatin solution used was dependent on the number of doses and number of beads/dose. The total number of oocysts in a single dose was approximately $1.5 \times 10^3$ oocysts.

The following examples are intended only to further illustrate the invention and are not intended to limit the scope of the invention as defined by the claims. Sporulated *Eimeria* oocysts for the control of coccidiosis in chickens and JELL-O flavored gelatin are used as a model system to illustrate the novel delivery system of the invention.

EXAMPLE 1

Gel beads were formed by heating approximately 25 ml. deionized water in a 50 ml heat resistant tube in a microwave to approximately 95-100 degrees C. After reaching the temperature range, approximately 14 grams of lime flavored JELL-O and approximately 4 grams of unflavored gelatin was added to the hot water. The contents were allowed to completely dissolve, and then the mixture was cooled to approximately 35 degrees C. with continuous mixing on a orbital rotator. Sporulated *Eimeria* spp. oocysts were added to the 35 degree C. water-gelatin mixture as follows: approximately $4.5 \times 10^4$ *Eimeria acervulina* oocysts, approximately $1 \times 10^4$ *Eimeria maxima*, and approximately $4.5 \times 10^4$ *Eimeria tenella* oocysts. The oocysts-containing mixture was stirred for an additional 1 minute and then removed with a 25 ml pipet pre-warmed to approximately 37 degrees C. The *Eimeria* oocysts-gelatin solution was then slowly pipetted dropwise into ice-cold mineral oil in a 250-ml beaker that was slowly stirring by means of a stir-bar and a non-heated stir-plate. Gel beads approximately 5 mm in diameter formed immediately from each drop, and then settled to the bottom of the beaker. After all the oocyst-gelatin mixture had been formed into gel beads, the excess mineral oil was removed, the bead slurry was poured into a 50 ml polypropylene centrifuge tube, and stored at about 4 degrees C. until use as a vaccine.

EXAMPLE 2

The *Eimeria* oocysts-containing gel beads made in Example 1 were used as a vaccine against coccidiosis in newly hatched (<2 hour old) broiler chicks, breed-Heritage, (Longneckers Hatchery, Elizabethtown, Pa.). The chicks were either "spray-vaccinated with a mixture of approximately $4.5 \times 10^3$ *Eimeria acervulina* oocysts, approximately $1 \times 10^3$ *Eimeria maxima* oocysts, and $4.5 \times 10^3$ *Eimeria tenella* oocysts or were not treated until transported back to the poultry facility. The spray-vaccinated chicks were sprayed with an aqueous solution in approximately a 0.9 ml volume containing the numbers of *Eimeria* spp. oocysts as indicated above using a hand-held 300-ml sprayer. Vaccinated chicks were kept in a separate container from non-vaccinated chicks, and placed in different regions of the vehicle used for transport. Upon returning to the poultry facility, spray-vaccinated chicks were placed in a single cage of a Petersime starting unit (Petersime). Another 10 chicks were placed in a separate cage that contained 4-100 mm wide glass Petri dishes each containing standard poultry ration (crumbles, 24% protein) and each Petri dish contained approximately a quarter of the preparation described in Example 1.

Each dish received approximately 12 gel-beads which were spread by pouring onto the surface of poultry feed in the Petri dish. Another 10 chicks were each inoculated by oral gavage with a mixture of approximately $4 \times 10^3$ *Eimeria acervulina* oocysts, approximately $1 \times 10^3$ *Eimeria maxima* oocysts, and approximately $4.5 \times 10^3$ *Eimeria tenella* oocysts. Chicks were provided poultry feed and water ad libitum. At about 3 days of age, each chick in all three groups were moved to individual cages of a Petersime starter unit. Fecal droppings were collected into 250 ml polypropylene bottles between days 5-8. Deionized water was added to each bottle to saturate the fecal material, the total volume of water and fecal material was approximately 250 ml. The number of *Eimeria* oocysts produced between days 5-8 was measured as follows. After collection into the 250 ml bottles and saturation with water, the fecal material was incubated for about 2 days at approximately 4 degrees C. The bottles were shaken by hand about 2-3 times/day to disrupt the fecal material. From each fecal slurry, approximately 0.75 ml was removed to a 1.5 microcentrifuge tube which contained approximately 0.75 ml of an approximately 2M sucrose solution. The tubes were then vortexed for about 10-15 seconds, and two aliquots were loaded onto separate chambers of a McMaster slide using a wide-bore 1 ml pipet. The McMaster slides were incubated at room temperature for about 5-10 minutes to allow *Eimeria* oocysts to be counted. Duplicate counts were done for each sample by counting all *Eimeria* oocysts on a light microscope at 100× magnification.

At two weeks of age, chickens were housed in groups of 3-7/replicate and placed in individual cages of a Petersime finisher unit. At 4 weeks of age, all vaccinated chickens, and a control group of non-vaccinated chickens were given a challenge infection of a mixture of *Eimeria* spp oocysts at the following number of oocysts/challenge dose-approximately $1.5 \times 10^5$ *Eimeria acervulina* oocysts, approximately $1 \times 10^3$ *Eimeria maxima* oocysts, and approximately $2.5 \times 10^4$ *Eimeria tenella* oocysts. This challenge dose was chosen to achieve a 50% decrease in weight gain and significant increase in feed conversion ratio relative to non-infected control chickens. Another group of non-vaccinated chickens were not challenged with the *Eimeria* spp. oocysts to serve as non-challenged controls. Body weights of all chickens were measured on day of challenge infection, and 7 days later post-challenge in order to calculate weight gain during the peak infection period. Feed conversion ratio (FCR) was also calculated for each replicate by dividing average feed consumption by average weight gain during the infection period.

Mean oocyst output/chicken was compared between vaccinated groups using a two-way ANOVA (InStat Software Package). Mean weight gain and FCR was compared between groups using Duncan's multirange test (SAS, Carlyle, N.C.). Significant differences between means were considered when $P<0.05$. The correlation coefficient between oocysts output and weight gain was calculated using InStat. The vaccination and challenge experiments were conducted 3 times.

Mean *Eimeria* spp. oocyst output/chicken was approximately 100-fold greater ($P<0.05$) in chickens vaccinated with the mixture of *Eimeria* species oocysts by gel-beads compared to the gel spray technique as shown in FIG. 1. Oocysts output by gel-bead vaccinated chickens was not significantly different ($P>0.05$) from chickens vaccinated by oral gavage with *Eimeria* spp. oocysts (FIG. 1). The range of oocyst output in gel-bead (–), spray-vaccinated (–) and oral gavage (–) revealed greater uniformity in vaccine delivered by gel-bead and oral gavage compared to spray vaccination.

Figure 2:
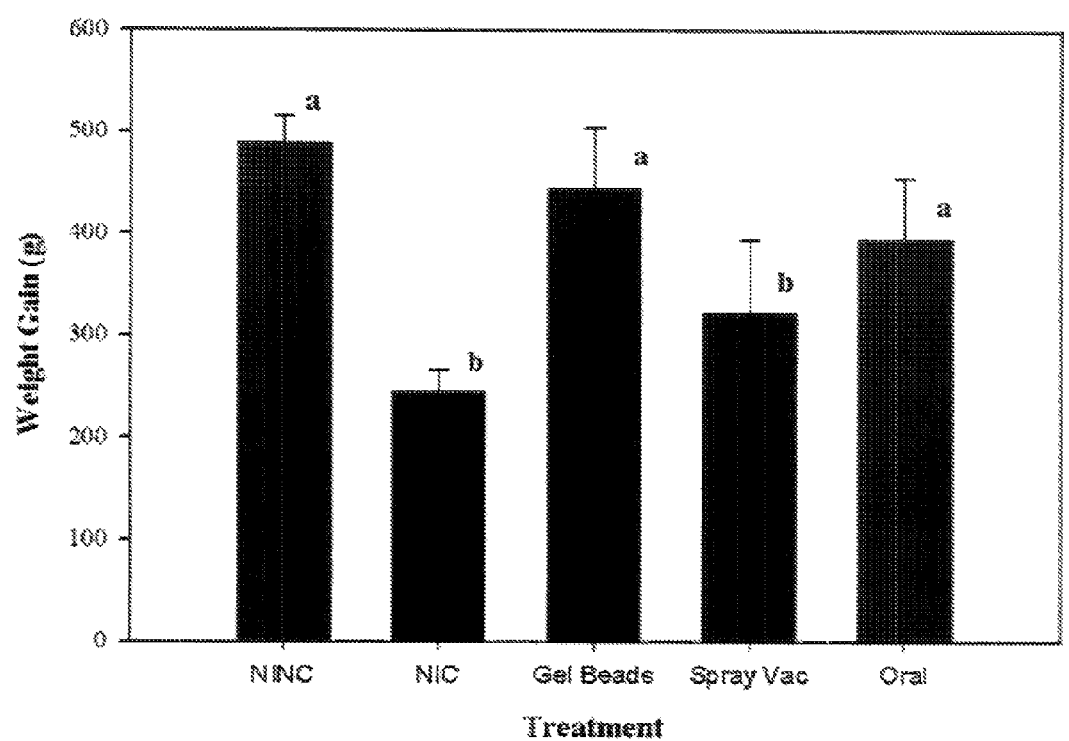
FIG. 2 is a graph showing average body weight gain over about a 7 day infection period in broiler chickens that were immunized at one-day of age with a mixture of *Eimeria acervulina, E. maxima*, and *E. tenella* oocysts by different delivery methods-gel-beads, spray-vaccination, or oral gavage, housed in battery cages, and then challenged at about 4 weeks of age with a high dose of *E. acervulina, E. maxima*, and *E. tenella* oocysts. The dose of *E. acervulina, E. maxima*, and *E. tenella* oocysts was such that weight gain in non-immunized control chickens receiving the *Eimeria* spp. oocysts challenge was 50% that of non-infected control chickens.

Mean weight gain in non-immunized, non-Eimeria challenged chickens (NINC, x=483±25 g) was over two-fold greater in non-immunized, *Eimeria* challenged chickens (NIC, x=241±17 g) indicating a highly virulent challenge infection (FIG. 2A). Chickens immunized with *Eimeria*-incorporated gel beads had mean weight gain that was not significantly different ($P>0.05$) from NINC controls or from chickens immunized by oral gavage with *Eimeria* oocysts (FIG. 2). However, chickens immunized by spray-vaccination showed significantly lower ($P<0.05$) weight gain compared to NINC, gel-bead immunized or oral gavage inoculated groups (FIG. 2)

Figure 3:
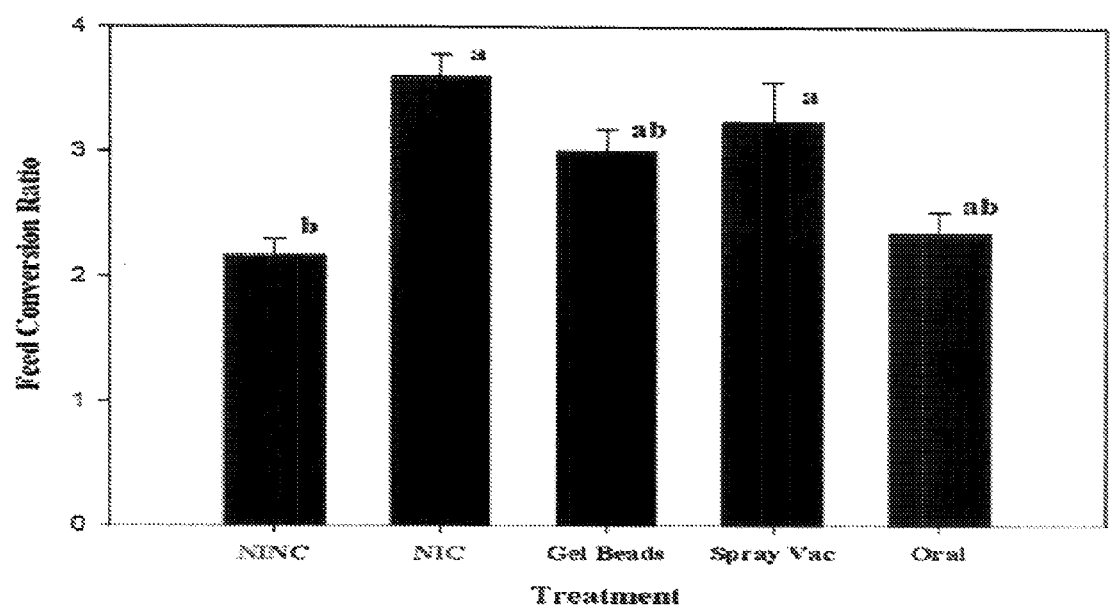
FIG. 3 is a graph showing average feed conversion ratio (FCR) over a 7 day infection period in broiler chickens that were immunized at one-day of age with a mixture of *Eimeria acervulina, E. maxima*, and *E. tenella* oocysts by different delivery methods-gel-beads, spray-vaccination, or oral gavage, housed in battery cages, and then challenged at about 4 weeks of age with a high dose of *E. acervulina, E. maxima*, and *E. tenella* oocysts. The dose of *E. acervulina, E. maxima*, and *E. tenella* oocysts was such that FCR in non-immunized control chickens receiving the *Eimeria* spp. oocysts challenge was significantly greater than FCR in non-infected control chickens.

Feed conversion ratio in non-immunized, non-Eimeria challenged control chickens (NINC, x=2.19±0.09) was significantly lower than in non-immunized, *Eimeria* challenged chickens (NIC, x=3.71±0.17) corroborating the weight gain data and severity of the challenge infection (FIG. 3). Chickens immunized with *Eimeria*-incorporated gel beads had mean FCR (x=2.81±0.18) that was not significantly different ($P>0.05$) from NINC controls (x=22.19±0.09) or from chickens immunized by oral gavage (x=2.35±0.16) with *Eimeria* oocysts (FIG. 3). However, chickens immunized by spray-vaccination showed significantly higher ($P<0.05$) FCR compared to NINC, gel-bead immunized, or oral gavage inoculated groups (FIG. 3).

EXAMPLE 3

Gel bead were prepared by mixing approximately 3.5 grams of a structuring agent, such as for example, bentonite clay with approximately 70 grams of a diluents such as, for example, deionized water, and heating to about 90 degrees centigrade. The mixture was then continually stirred and kept at a constant temperature to maintain a temperature of approximately 60 degrees C. After reaching 60 degrees C., approximately 13 grams of bovine gelatin (Sigma Cat. No. G9382), approximately 30 grams glycerin and 1 drop of green food dye were added. After the contents dissolved, an aliquot of the mixture was removed and allowed to cool to approximately 40 degrees centigrade. Approximately $1.5 \times 10^3$ sporulated oocysts from cyst forming protozoa were added, suspended in a volume of approximately 0.1 ml of the aliquot removed from the mixture and then added back to the approximately 40 degree C. gel solution, mixed by rapid inversion and inoculated drop-wise into ice-cold vegetable or mineral oil using a syringe and a 20-gauge needle. Approximately 10% of the total number of oocysts was *E. maxima*, and *E. acervulina* and *E. tenella* were each at 45% of the total number of oocysts. The overlaying mineral oil was poured off, and the gel beads transferred to a 50 ml polypropylene test tube, and stored at about 4 degrees C. until use.

EXAMPLE 4

Newly-hatched broiler chickens (Heritage breed, Longeneckers Hatchery, Elizabethtown, Pa.) were placed in cages of a Petersime brooder unit at 6 chicks/cage. Gel beads containing *Eimeria* oocysts were spread onto standard poultry ration feed in two 100 mm-wide glass Petri dishes and placed on chick transport paper inside the cage. Separate groups of chicks were given the same number of oocysts at either 25 beads/dose or 50 beads/dose. A control group of chicks received an equivalent number of *Eimeria* spp. oocyst by oral gavage to serve as a positive control for infection. Chicks were provided feed and water ad libitum. After 3 days, each chick was transferred to an individual cage of a Petersime brooder unit. At 5 days, droppings paper was removed from below each cage, collection pans sprayed with non-stick vegetable oil, and fecal material collected between days 5-8 post-hatch. Feces from each chick were transferred to plastic 250 ml polypropylene bottles, and water added to 250 ml. The fecal material-water mixture in each 250 ml bottle was placed at refrigerator temperatures. At 4 weeks of age, all chickens were wing-banded and transferred to individual cages of a Petersime finisher unit at 3 chickens/cage with 2 replicates/treatment. All chickens were challenged with a high dose of a mixture of *E. acervulina* ($1.5 \times 10^5$), *E. maxima* ($1.0 \times 10^3$), and *E. tenella* ($1.0 \times 10^4$) oocysts. Control groups consisted of an equal number of the same age and breed of non-vaccinated chickens that were either challenged (NIC) or not challenged (NINC) with the *Eimeria* oocysts mixture. Body weights of all chickens were measured on day of challenge, and at termination 7 days later. Feed conversion ratio (FCR) was calculated for all groups by measuring the average amount of feed consumed over the infection period, and dividing this value by the average weight gain in each group.

Figure 4:
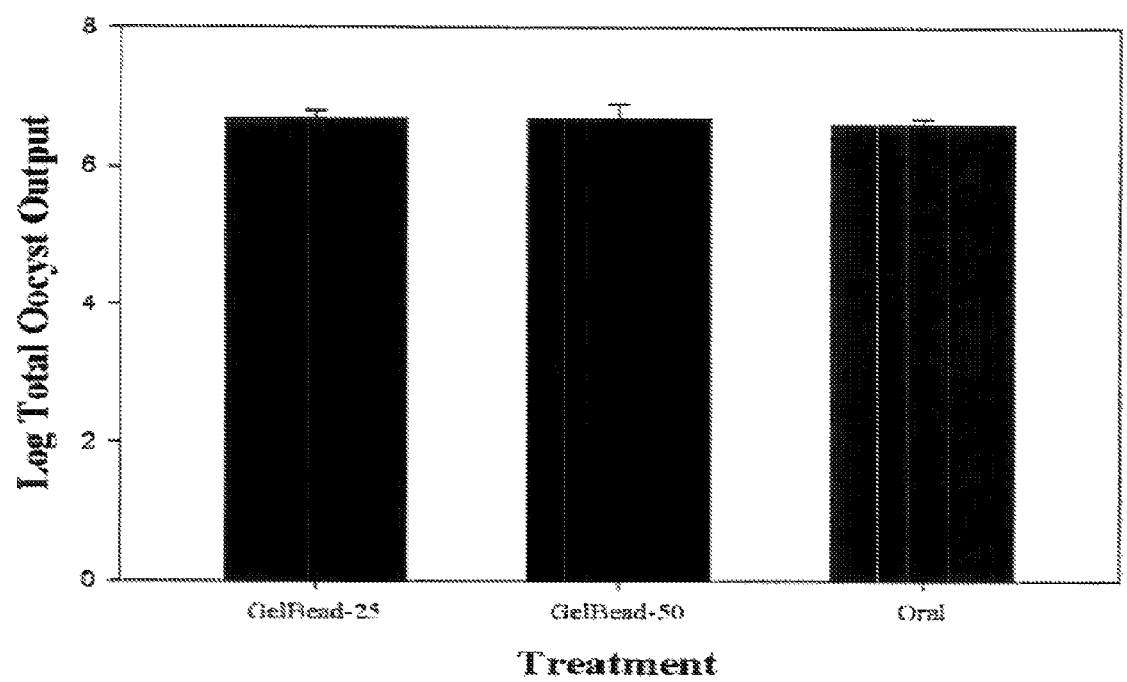
FIG. 4 is a graph showing average total *Eimeria* oocyts output between days 5-8 post-immunization in week-old broiler chickens vaccinated with a mixture of *Emieria acervulina, Eimeria maxima*, and *Eimeria tenella* oocysts delivered by gelatin beads containing Bentonite clay, and applied at either 25- or 30-beads/dose. Production of oocysts arising from oral gavage of an identical number of oocysts represents a positive vaccine control.
Figure 5:
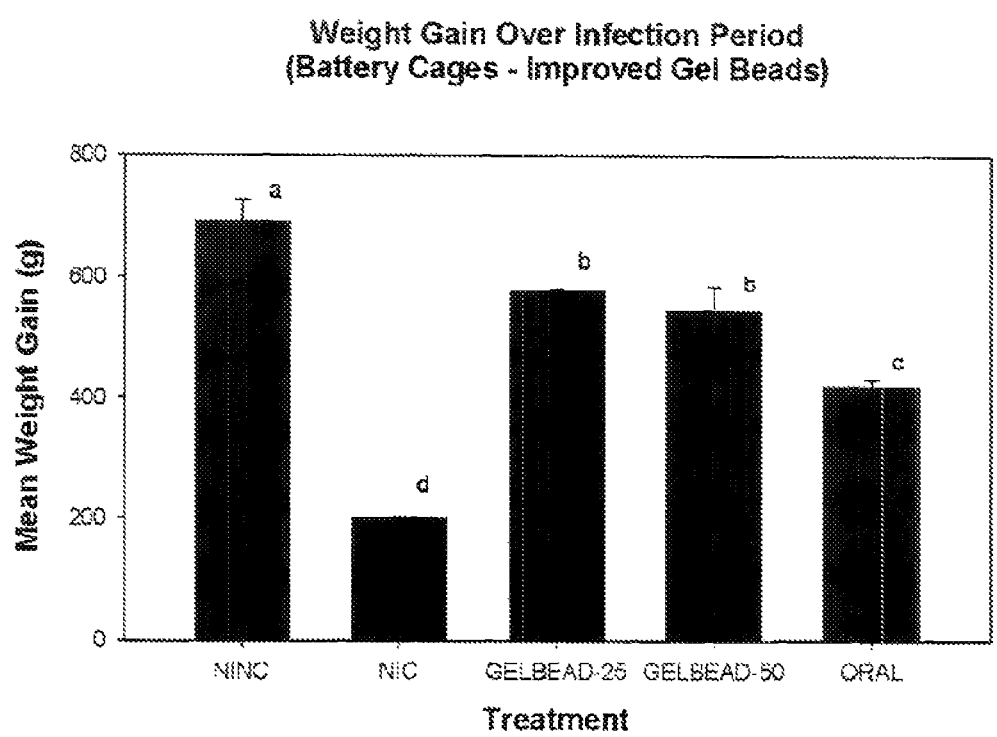
FIG. 5 is a graph showing average body weight gain over about a 7 day infection period in broiler chickens that were immunized at one-day of age with a mixture of *Eimeria acervulina, E. maxima*, and *E. tenella* oocyts by gelatin beads containing Bentonite clay, and applied at either 25- or 50-beads/dose or by oral gavage using an identical number of *Eimeria* oocysts, housed in battery cages, and then challenged at about 4 weeks of age with a high dose of *E. acervulina, E. maxima*, and *E. tenella* oocysts. The dose of *E. acervulina, E. maxima*, and *E. tenella* oocysts was such that weight gain in non-immunized control chickens receiving the *Eimeria* spp. oocysts challenge was approximately 30% that of non-infected control chickens.
Figure 6:
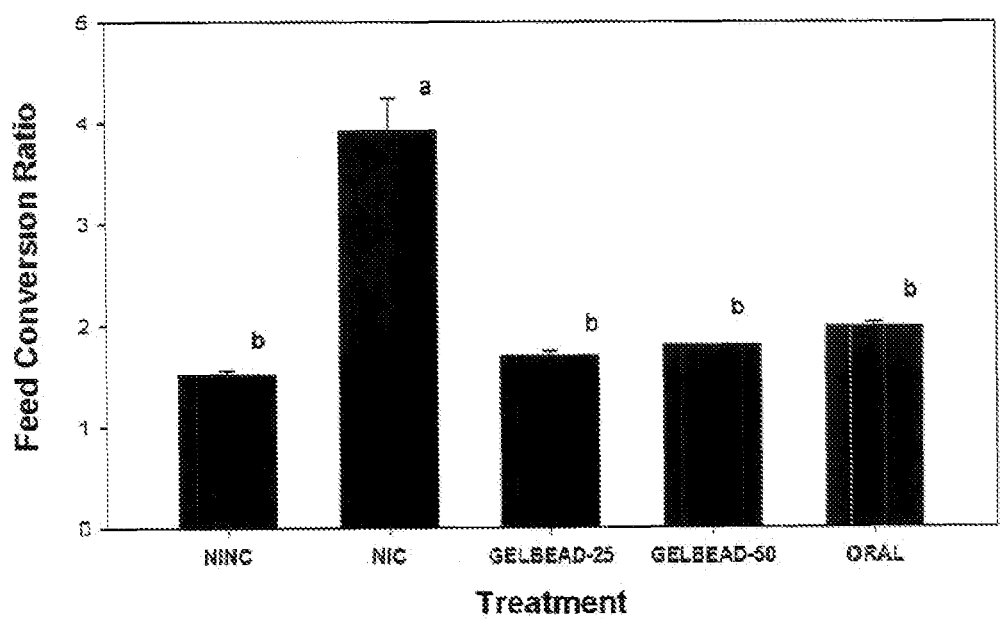
FIG. 6 is a graph showing average feed conversion ratio (FCR) over a 7 day infection period in broiler chickens that were immunized at one-day of age with a mixture of *Eimeria acervulina, E. maxima*, and *E. tenella* oocysts by gelatin beads containing Bentonite clay, and applied at either 25- or 50-beads/dose or by oral gavage using an identical number of *Eimeria* oocystgs, housed in battery cages, and then challenged at about 4 weeks of age with a high dose of *E. acervulina, E. maxima*, and *E. tenella* oocysts. The dose of *E. acervulina, E. maxima*, and *E. tenella* oocysts was such that FCR in non-immunized control chickens receiving the *Eimeria* spp. oocysts challenge was significantly greater than FCR in non-infected chickens.

Chicks vaccinated with a mixture of *E. acervulina, E. maxima*, and *E. tenella* oocysts at 25 beads/dose or 50 beads/dose produced an identical number of *Eimeria oocysts* (log 6.7) which was not significantly different (P>0.05) from those given the same *Eimeria* spp. mixture by oral gavage (FIG. 4 "Oocyst Output Post-Vaccination Battery Cages-Improved Gel Beads"). The coefficient of variation (SD/mean) in the gel beads groups (25 beads/dose=1.5%, 50 beads/dose=3.0%) was similar to the COV in oral gavage groups (1.5%) suggesting that *Eimeria* oocysts were not affected by the gel preparation method, and that the uniformity in uptake was similar to oral gavage. Although less than the non-challenged controls (NINC), mean weight gain in chicks vaccinated with *Eimeria* oocysts in gel beads (25 beads/dose and 50 beads/dose) was significantly greater than weight gain in the non-vaccinated challenged controls (NIC, FIG. 5, "Weight Gain Over Infection Period Battery Cages-Improved Gel Beads"). In fact, weight gain in chickens receiving *Eimeria* oocysts in gel beads was significantly greater than the positive control (ORAL, FIG. 5). Feed conversion ratios in both *Eimeria* gel bead groups (25 beads/dose, 50 beads/dose) and in the positive control (ORAL) showed no significant difference from the non-vaccinated non-challenged controls (NINC, FIG. 6, "Feed Conversion Ratio Over Infection Period Battery Cages-Improved Gel Beads"). All vaccinated groups showed a significant improvement in FCR over the non-vaccinated, *Eimeria* challenged group (NIC, FIG. 6). These findings indicate that vaccinating day-old chicks with a mixture of *Eimeria* spp. oocysts suspended in gel beads confers a level of protection that is equal to oral gavage.

Weight gain, and feed conversion ratios and log of total oocyts output in all experiments were analyzed using one-way ANOVA (SigmaPlot 11, Systat Software, Inc., San Jose, Calif.). Significant differences (P<0.05) between means were determined using Duncan's Multi-Range test (SAS Institute, Cary, N.C.).

EXAMPLE 5

Newly-hatched broiler chickens (Heritage breed, Longeneckers Hatchery, Elizabethtown, Pa.) were placed in floor pen cages (75 cm wide×140 cm long×55 cm high) at 15 chicks/cage. The cages were set in stainless steel pans, and wood shavings covered the entire floor of each cage. Gel beads containing *Eimeria* oocysts were spread onto standard poultry ration feed in one 30 cm×30 cm square pan, and place on the floor of the cage. Separate groups of chicks were given the same number of oocysts at either 25 beads/dose or 50 beads/dose. A control group of chicks received an equivalent number of *Eimeria* spp. oocyst by oral gavage to serve as a positive control for infection. Chicks were provided feed and water ad libitum. At 4 weeks of age, all chickens were wing-banded and challenged with a high dose of a mixture of *E. acervulina* ($1.5 \times 10^5$), *E. maxima* ($1.0 \times 10^3$), and *E. tenella* ($1.0 \times 10^4$) oocysts. Control groups consisted of an equal number of the same age and breed of non-vaccinated chickens that were either challenged (NIC) or not challenged (NINC) with the *Eimeria* oocysts mixture. Body weights of all chickens were measured on day of challenge, and at termination 7 days later.

Figure 7:
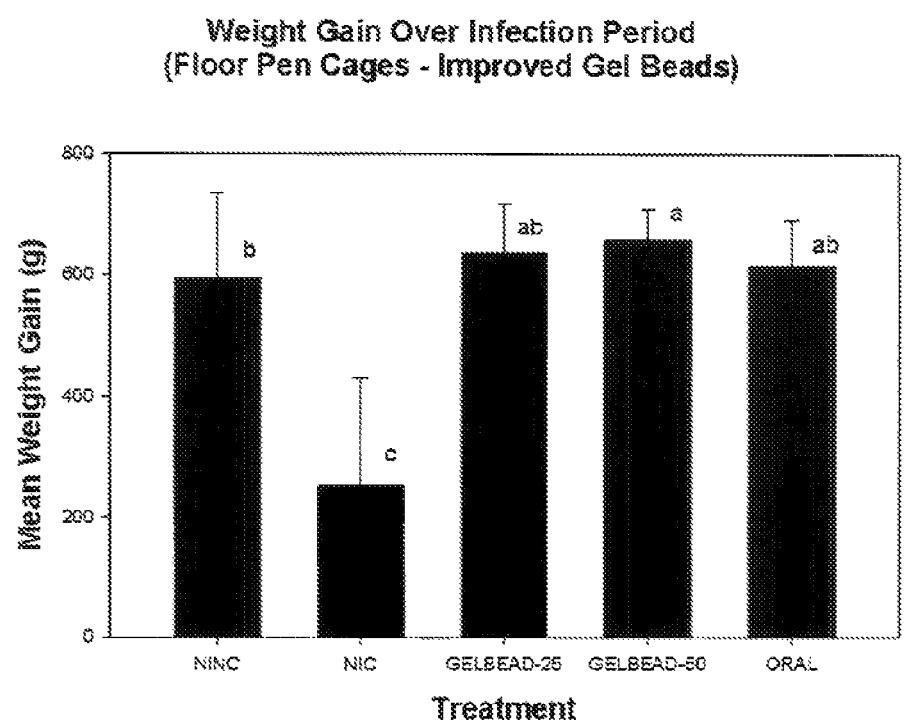
FIG. 7 is a graph showing average body weight gain over about a 7 day infection period in broiler chickens that were immunized at one-day of age with a mixture of *E. acervulina, E. maxima*, and *E. tenella* oocysts by gelatin beads containing Bentonite clay, and applied at either 25- or 50-beads/dose or by oral gavage using an identical number of *Eimeria* oocysts, housed in floor pen cages, and then challenged at about 4 weeks of age with a high dose of *E. acervulina, E. maxima*, and *E. tenella* oocysts. The dose of *E. acervulina, E. maxima*, and *E. tenella* oocysts was such that weight gain in non-immunized control chickens receiving the *Eimeria* spp. oocysts challenge was approximately 43% that on non-infected control chickens.

Chickens vaccinated with a mixture of *E. acervulina, E. maxima*, and *E. tenella* oocysts at 25 beads/dose or 50 beads/dose displayed a significant increase in weight gain compared to non-vaccinated *Eimeria* challenged controls (NIC, FIG. 7, "Weight Gain Over Infection Period Floor Pen Cages-Improved Gel Beads"). This weight gain was not significantly different from the non-vaccinated non-*Eimeria* challenged controls (NINC, FIG. 7). These findings indicate that vaccinating day-old chicks with a mixture of *Eimeria* spp. oocysts suspended in gel beads and placing the chicks on floor pens confers complete protection against a high dose *Eimeria* spp. challenge. The higher level of protection observed in the floor pen study is probably due to the phenomenon of "recycling", that is chickens re-ingesting shed *Eimeria* oocysts, which leads to a more solid immunity. Cycling is not possible in battery cages because chickens are raised on wire in suspended cages, and thus do not have access to fecal material containing *Eimeria* oocysts.

Weight gain, and feed conversion ratios and log of total oocyts output in all experiments were analyzed using one-way ANOVA (SigmaPlot 11, Systat Software, Inc., San Jose, Calif.). Significant differences (P<0.05) between means were determined using Duncan's Multi-Range test (SAS Institute, Cary, N.C.).

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention.

We claim:

1. A vaccine delivery system comprising a gel bead made with a gelatin in amounts effective to make a storable gel bead, and includes a diluent, a humectant, a structuring agent, and oocysts from at least one cyst-forming protozoa in amounts effective to induce at least partial immunity in a vaccinated animal, wherein said structuring agent is selected from the group consisting of bentonite, montmorillonite, attapulgite, terramine, saponite, French-green clay, Fuller's earth, silicates, metal salts, and mixtures thereof.

2. The vaccine delivery system of claim 1 wherein said gelatin is selected from the group consisting of flavored gelatin, unflavored gelatin, and mixtures thereof.

3. The vaccine delivery system of claim 1 wherein said humectants is selected from the group consisting of glycerin, a sugar alcohol, propylene glycol, polyglycols and mixtures thereof.

4. The vaccine of claim 1 further comprising an edible coating selected from the group consisting of methylmethacrylates, zein, cellulose derivatives, fats, waxes and mixtures thereof.

5. The vaccine delivery system of claim 1 wherein said oocysts are from protozoa of the genus *Eimeria*.

6. A method for vaccinating animals for disease caused by cyst-forming protozoa comprising providing an effective amount of an edible oocyst-containing gel bead vaccine to an animal susceptible to said disease wherein said effective amount is an amount effective to reduce the severity of said disease caused by said protozoa in said animal wherein said vaccine is the vaccine delivery system of claim 1.

7. A method for vaccinating animals for disease caused by cyst-forming protozoa comprising providing an effective amount of an edible oocyst-containing gel bead vaccine to an animal susceptible to said disease wherein said effective amount is an amount effective to reduce the severity of said disease caused by said protozoa in said animal wherein said vaccine is the vaccine delivery system of claim 2.

8. A method for vaccinating animals for disease caused by cyst-forming protozoa comprising providing an effective amount of an edible oocyst-containing gel bead vaccine to an animal susceptible to said disease wherein said effective amount is an amount effective to reduce the severity of said disease caused by said protozoa in said animal wherein said vaccine is the vaccine delivery system of claim 3.

9. A method for vaccinating animals for disease caused by cyst-forming protozoa comprising providing an effective amount of an edible oocyst-containing gel bead vaccine to an animal susceptible to said disease wherein said effective amount is an amount effective to reduce the severity of said disease caused by said protozoa in said animal wherein said vaccine is the vaccine delivery system of claim 4.

10. A method for vaccinating animals for disease caused by cyst-forming protozoa comprising providing an effective amount of an edible oocyst-containing gel bead vaccine to an animal susceptible to said disease wherein said effective amount is an amount effective to reduce the severity of said disease caused by said protozoa in said animal wherein said vaccine is the vaccine delivery system of claim 5.

11. The method of claim 6 wherein said animal is a domesticated bird.

12. The method of claim 11 wherein said domesticated bird is in the order Galliformes.

13. The method of claim 11 wherein said domesticated bird is selected from the group consisting of chicken, turkey, goose, and ducks.

14. The method of claim 6 wherein said structuring agent of said vaccine delivery system of claim 1 is bentonite.

15. The method of claim 14 wherein said humectants of said vaccine delivery system is glycerin.

16. The method of claim 15 wherein said protozoa are *Eimeria* spp. and wherein said animal is a domesticated bird.

17. The method of claim 15 wherein said oocysts are from *E. acervulina, E. maxima, E. tenella, E. necatrix, E. brunette*, or *E. praecox*, or a combination thereof and wherein said animal is a domesticated bird.

18. The vaccine delivery system of claim 1 wherein said structuring agent is bentonite.

19. The vaccine delivery system of claim 18 wherein said humectant is glycerin.

20. The vaccine delivery system of claim 19 wherein said protozoa is *Eimeria* spp.

21. The vaccine delivery system of claim 19 wherein said oocysts are from *E. acervulina, E. maxima, E. tenella, E. necatrix, E. brunette*, or *E. praecox*, or a combination thereof.

22. A vaccine delivery system comprising a gel bead made with a gelatin in amounts effective to make a storable gel bead, and includes a diluent, a humectant, a structuring agent, and oocysts from at least one cyst-forming protozoa in amounts effective to induce at least partial immunity in a vaccinated animal, wherein said structuring agent is selected from the group consisting of bentonite, montmorillonite, attapulgite, terramine, saponite, French-green clay, Fuller's earth, silicates, metal salts, and mixtures thereof, and wherein the concentration of said gelatin, based on solids, is at 30% or higher.

23. The vaccine delivery system of claim 22 wherein said gelatin is selected from the group consisting of flavored gelatin, unflavored gelatin, and mixtures thereof.

24. The vaccine delivery system of claim 22 wherein said humectants is selected from the group consisting of glycerin, a sugar alcohol, propylene glycol, polyglycols and mixtures thereof.

25. The vaccine of claim 22 further comprising an edible coating selected from the group consisting of methylmethacrylates, zein, cellulose derivatives, fats, waxes and mixtures thereof.

26. The vaccine delivery system of claim 22 wherein said oocysts are from protozoa of the genus *Eimeria*.

27. The vaccine delivery system of claim 22 wherein said structuring agent is bentonite.

28. The vaccine delivery system of claim 27 wherein said humectant is glycerin.

29. The vaccine delivery system of claim 28 wherein said protozoa is *Eimeria* spp.

30. The vaccine delivery system of claim 28 wherein said oocysts are from *E. acervulina, E. maxima, E. tenella, E. necatrix, E. brunette*, or *E. praecox*, or a combination thereof.

31. A method for controlling a disease caused by a cyst-forming protozoa in an animal susceptible to said disease comprising providing an effective amount of the vaccine delivery system of claim 22 to said animal, wherein said effective amount is an amount effective to reduce the severity of said disease in said animal, and wherein said animal is a domesticated bird.

32. The method of claim 31 wherein said domesticated bird is in the order Galliformes.

33. The method of claim 31 wherein said domesticated bird is selected from the group consisting of chicken, turkey, goose, and ducks.

34. The method of claim 31 wherein said structuring agent of said vaccine delivery system is bentonite.

35. The method of claim 34 wherein said humectant of said vaccine delivery system is glycerin.

36. The method of claim 35 wherein said protozoa is *Eimeria* spp.

37. The method of claim 35 wherein said oocysts are from *E. acervulina, E. maxima, E. tenella, E. necatrix, E. brunette*, or *E. praecox*, or a combination thereof.

38. A method for controlling a disease caused by a cyst-forming protozoa in an animal susceptible to said disease comprising providing an effective amount of the vaccine delivery system of claim 23 to said animal, wherein said effective amount is an amount effective to reduce the severity of said disease in said animal, and wherein said animal is a domesticated bird.

39. A method for controlling a disease caused by a cyst-forming protozoa in an animal susceptible to said disease comprising providing an effective amount of the vaccine delivery system of claim 24 to said animal, wherein said effective amount is an amount effective to reduce the severity of said disease in said animal, and wherein said animal is a domesticated bird.

40. A method for controlling a disease caused by a cyst-forming protozoa in an animal susceptible to said disease comprising providing an effective amount of the vaccine delivery system of claim 25 to said animal, wherein said effective amount is an amount effective to reduce the severity of said disease in said animal, and wherein said animal is a domesticated bird.

41. A method for controlling a disease caused by a cyst-forming protozoa in an animal susceptible to said disease comprising providing an effective amount of the vaccine delivery system of claim 26 to said animal, wherein said effective amount is an amount effective to reduce the severity of said disease in said animal, and wherein said animal is a domesticated bird.

42. A method for controlling a disease caused by a cyst-forming protozoa in an animal susceptible to said disease comprising providing an effective amount of the vaccine delivery system of claim 27 to said animal, wherein said effective amount is an amount effective to reduce the severity of said disease in said animal, and wherein said animal is a domesticated bird.

* * * * *